(12) United States Patent
Takebayashi

(10) Patent No.: US 7,820,686 B2
(45) Date of Patent: Oct. 26, 2010

(54) THERAPEUTIC AGENT FOR INFLAMMATORY BOWEL DISEASE

(75) Inventor: Yuji Takebayashi, Fukushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/296,671

(22) PCT Filed: Apr. 12, 2007

(86) PCT No.: PCT/JP2007/000403
§ 371 (c)(1),
(2), (4) Date: Oct. 10, 2008

(87) PCT Pub. No.: WO2007/122812
PCT Pub. Date: Nov. 1, 2007

(65) Prior Publication Data
US 2009/0209565 A1     Aug. 20, 2009

(30) Foreign Application Priority Data
Apr. 13, 2006   (JP) .............................. 2006-110869

(51) Int. Cl.
*A61K 31/506* (2006.01)
(52) U.S. Cl. .................................................. 514/274
(58) Field of Classification Search ........................ None
See application file for complete search history.

(56) References Cited

U.S. PATENT DOCUMENTS

| 5,744,475 A | 4/1998 | Yano et al. |
| 6,479,500 B1 | 11/2002 | Fukushima et al. |

2001/0016214 A1   8/2001   Kanauchi et al.

FOREIGN PATENT DOCUMENTS

| EP | 1 080 726 A1 | 3/2001 |
| WO | 96 30346 | 10/1996 |
| WO | 97 37674 | 10/1997 |
| WO | 98 13045 | 4/1998 |
| WO | 2000 56337 | 9/2000 |

OTHER PUBLICATIONS

Zou et al., Journal of Tongji Medical University, 21(4), (2001), pp. 308-309.*
Stephan R. Targan, et al., "A short-term study of Chimeric Monoclonal Antibody cA2 to Tumor Necrosis Factor α for Crohn's Disease", The New England Journal of Medicine, Oct. 9, 1997, vol. 337, No. 15, pp. 1029-1035.
Paul Rutgeerts, et al., "Efficacy and Safety of Retreatment With Anti-Tumor Necrosis Factor Antibody (Infliximab) to Maintain Remission in Crohn's Disease", Gastroenterology, 1999, vol. 117, No. 4, pp. 761-769.

* cited by examiner

*Primary Examiner*—Phyllis G. Spivack
(74) *Attorney, Agent, or Firm*—Oblon, Spivak, McClelland, Maier & Neustadt, L.L.P.

(57) ABSTRACT

The invention is directed to a method of treating an inflammatory bowel disease such as ulcerative colitis or Crohn's disease, which comprises administering an effective amount of the therapeutic agent 5-chloro-6-(2-iminopyrrolidin-1-yl) methyl-2,4(1H,3H)-pyrimidinedione, or a pharmaceutically acceptable salt thereof, to a patient with inflammatory bowel disease.

3 Claims, 4 Drawing Sheets

Control

TNBS

TNBS + Compound (1)

THERAPEUTIC AGENT FOR INFLAMMATORY BOWEL DISEASE

TECHNICAL FIELD

The present invention relates to a therapeutic agent for inflammatory bowel disease.

BACKGROUND ART

Inflammatory bowel disease (IBD) is an incurable idiopathic disease in which chronic inflammation or ulceration at the mucous membrane of the large and small intestines is caused, and diarrhea or bloody stool continues over a long period with recurrence repeated. This disease is designated as one of the specified diseases in Japan, and a medical care certificate is issued to each patient under the research project for the disease. IBD includes two major types of diseases, that is, Crohn's disease (CD) and ulcerative colitis (UC).

Crohn's disease, which is also called regional enteritis, granulomatous ileitis or ileocolitis, is a chronic inflammation developed on the intestinal wall, or even on any site of the digestive tract. Ulcerative colitis is a chronic disease wherein inflammation occurs in the large intestine to produce an ulcer, resulting in bloody diarrhea, severe abdominal pain, or an attack accompanied with fever. The numbers of the patients of the two diseases are on increase in Japan though they are not higher than those in Europe or the United States. In particular, the numbers of the patients were about 73,000 (in the year 2001) for ulcerative colitis, and about 21,000 (in the year 2001) for Crohn's disease. Furthermore, the number of the medical care certificates issued for ulcerative colitis was ranked on the first place, and the number issued for Crohn's disease was ranked on the eighth place among the 46 specified diseases.

Since the cause of inflammatory bowel disease is unknown as described above, conventional therapeutic agents for diarrhea and the like are not effective. For the treatment of inflammatory bowel disease, aminosalicylic acid preparations (sulfasalazine, 5-aminosalicylic acid) and corticosteroid preparations have been widely used from the past as first-line and second-line drugs. In addition, in a severe case, immunosuppressants (azathioprine, 6-mercaptopurine, and the like), and anti-cytokine preparations have been used. Sulfasalazine and 5-aminosalicylic acid are widely used as an aminosalicylic acid preparation, however, in about 50% of the patients administered with them, they cause digestive organ disorders such as nausea, vomiting, anorexia and hepatic function disorders, and blood system disorders such as agranulocytosis, hemolytic anemia, and folic acid deficiency anemia. Furthermore, since they have salicylic acid skeleton, they are likely to manifest adverse effects in a case that shows hypersensitive reaction to salicylic acid-based drugs, and may cause diarrhea, abdominal pain, amylase increase, renal disorders and the like. Sulfasalazine may cause adverse effects such as male infertility and colored urine, which may become great mental stresses as well to the patients. Corticosteroid preparations have various adverse effects such as osteoporosis, growth impairment, secondary adrenal insufficiency, glucose intolerance, and hypertension. Furthermore, they also have a problem that they have no effects of maintaining the remission of CD or UC. On the other hand, the anti-cytokine therapy is new and totally different from such conventional ones, and the drug that first came out is infliximab which is a chimeric anti-human TNF-α monoclonal antibody. It has been reported that it is effective for the patients with Crohn's disease who have steroid resistance rated as moderate to severe (Non-patent Document 1), and that it is also effective for maintaining the remission (Non-patent Document 2). Adverse effects of it such as hypertension, nausea, rash, fever, headache, and eczema are known. Furthermore, since infliximab is a chimeric antibody, it may show antigenicity, and sometimes cause acute ultra-hypersensitive reaction. Furthermore, recently, infection such that it needs antibiotics or carcinogenicity becomes issues.

[Non-patent Document 1] N. Engl. J. Med., Vol. 337, page 1029,
[Non-patent Document 2] Gastroenterology, Vol. 117, page 761, 1999

DISCLOSURE OF THE INVENTION

Problems to be Solved by the Invention

The object of the present invention is to provide a novel therapeutic agent for inflammatory bowel disease.

Means for Solving the Problems

The present inventor has investigated therapeutic effects of various compounds on inflammatory bowel disease using 2,4,6-trinitrobenzene sulfonic acid (TNBS)-induced and dextran sulfate sodium (DSS) induced IBD models, which are known as models for inflammatory bowel disease. As a result, the present inventor has found unexpectedly that 5-chloro-6-(2-iminopyrrolidin-1-yl)methyl-2,4(1H,3H)-pyrimidinedione hydrochloride [Compound (1)], which has been known to have potentiating actions on anti-tumor effects, inhibitory actions on cancer metastasis, and alleviating actions on adverse effects of anti-tumor agents, has excellent therapeutic effects on inflammatory bowel disease, and thus completed the present invention.

In other words, the present invention provides a therapeutic agent for inflammatory bowel disease containing 5-chloro-6-(2-iminopyrrolidin-1-yl)methyl-2,4(1H,3H)-pyrimidinedione [compound (I)] or a pharmaceutically acceptable salt thereof as an active ingredient.

The present invention also provides use of 5-chloro-6-(2-iminopyrrolidin-1-yl)methyl-2,4(1H,3H)-pyrimidinedione or a pharmaceutically acceptable salt thereof for preparation of a therapeutic agent for inflammatory bowel disease.

The present invention also provides a method of treating inflammatory bowel disease, which includes administering an effective amount of 5-chloro-6-(2-iminopyrrolidin-1-yl)methyl-2,4(1H,3H)-pyrimidinedione or a pharmaceutically acceptable salt thereof.

Effects of the Invention

According to the present invention, an effective and safe therapeutic agent for inflammatory bowel disease including ulcerative colitis and Crohn's disease can be provided. The balance between the therapeutic effect on a chronic inflammation such as inflammatory bowel disease and the adverse side effect of Compound (1) is superior to those of an aminosalicylic acid preparation and a corticosteroid preparation, which cannot be expected at all from a mere anti-diarrheal effect.

Figure 1:
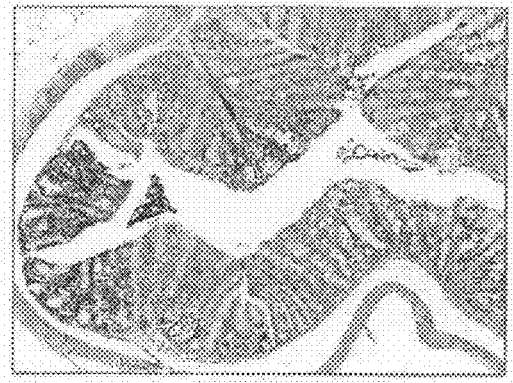
FIG. 1 is a HE-staining figure showing an inhibitory action of inflammation by administration of Compound (1) in TNBS-induced colitis mouse.
Figure 1:
Figure 1:
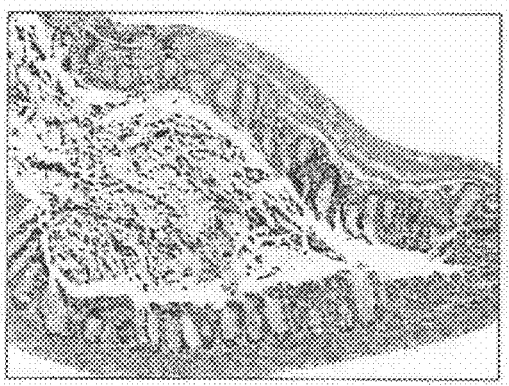

BEST MODE FOR CARRYING OUT THE INVENTION 5-chloro-6-(2-iminopyrrolidin-1-yl)methyl-2,4(1H,3H)-pyrimidinedione, which is used as an active ingredient in the present invention, is a compound represented by the following formula (I).

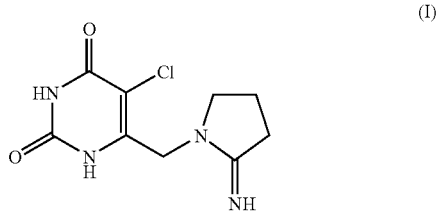

(I)

Compound (I), which is a known compound, is known to have pharmacological actions such as potentiating actions on anti-tumor effects (WO/9630346), inhibitory actions on cancer metastasis (WO/9813045), and alleviating actions on adverse effects of anti-tumor agents (JP-A-2000-273044). However, no action of Compound (I) on inflammatory bowel disease has been known.

The pharmaceutically acceptable salt of Compound (I) is not particularly limited, however, an acid addition salt is preferred, in which a pharmaceutically acceptable acid is added. Examples of the acid addition salt include a salt with an inorganic acid such as hydrochloric acid, sulfuric acid, phosphoric acid, or hydrobromic acid; and a salt with an organic acid such as oxalic acid, maleic acid, fumaric acid, malic acid, tartaric acid, citric acid, benzoic acid, acetic acid, p-toluenesulfonic acid, or methanesulfonic acid. Of these, a salt with hydrochloric acid or p-toluenesulfonic acid is preferred. Particularly preferred specific examples of Compound (I) or a salt thereof are 5-chloro-6-(2-iminopyrrolidin-1-yl)methyl-2,4(1H,3H)-pyrimidinedione hydrochloride and 5-chloro-6-(2-iminopyrrolidin-1-yl)-2,4(1H,3H)-pyrimidinedione p-toluenesulfonic acid salt.

Compound (I) or a salt thereof has very excellent anti-inflammatory actions and inhibitory actions of apoptosis in intestinal epithelial cells in TNBS-induced or DSS-induced IBD model that is known as a model for inflammatory bowel disease, as shown below in Examples. Such therapeutic effects are superior to those of a corticosteroid preparation, which has been conventionally used for IBD. Furthermore, Compound (I) or a salt thereof has high safety, and is useful as a novel therapeutic agent for inflammatory bowel disease if considered the fact that conventional therapeutic agents for inflammatory bowel disease have the problems of numerous adverse effects.

Although Compound (I) or a salt thereof is known as a thymidine phosphorylase inhibitor, thymidine phosphorylase is substantially not expressed in the digestive tract of rodents such as mice and rats which have been used in the Examples. Thus, it is hardly considered that Compound (I) exerts the therapeutic effects on inflammatory bowel disease simply by the thymidine phosphorylase inhibitory actions. In addition, although it is also known that Compound (I) has inhibitory effects on diarrhea caused by anti-tumor agents, this only discloses inhibitory effects on cell damage by the anti-tumor agents. Thus, from such findings, therapeutic effects on chronic inflammatory diseases as in the present invention cannot be expected at all. In addition, since thymidine phosphorylase is known to induce angiogenesis by the activity as PD-ECGF, there has been reported that a thymidine phosphorylase inhibitor is used as a cancer metastasis inhibitor by the angiogenesis inhibitory actions. However, it is unknown that the thymidine phosphorylase inhibitor is useful as a therapeutic agent for inflammatory bowel disease.

The disease of interest in the present invention includes inflammatory bowel disease such as Crohn's disease, ulcerative colitis, collagenous colitis, lymphocytic colitis, and bypass colitis, particularly, Crohn's disease and ulcerative colitis.

Compound (I) or a salt thereof may be formulated into various dosage forms, respectively, and administered.

When the medication according to the present invention is used as a therapeutic agent for IBD in mammals including human, it may be formulated into various pharmaceutical dosage forms depending on the therapeutic purpose. In particular, examples of the form include oral agents such as tablets, coated tablets, pills, powders, granules, capsules, solutions, suspensions, and emulsions; and parenteral agents such as injections, and suppositories. The aforementioned preparations can be manufactured with a pharmaceutically acceptable carrier according to commonly used methods for formulation. The tablets may be prepared by using, as carriers, for example, excipients such as lactose, sucrose, sodium chloride, glucose, urea, starch, calcium carbonate, kaoline, crystalline cellulose, and silicic acid; binders such as water, ethanol, propanol, cornstarch, simple syrup, glucose solution, starch solution, gelatin solution, carboxymethylcellulose, shellac, methylcellulose, hydroxypropylcellulose, hydroxypropylmethylcellulose, potassium phosphate, and polyvinylpyrrolidone; disintegrators such as dried starch, sodium alginate, agar powder, laminaran powder, sodium bicarbonate, calcium carbonate, polyoxyethylene sorbitan fatty acid esters, sodium lauryl sulfate, stearic acid monoglyceride, and lactose; disintegration suppressing agents such as sucrose, stearic acid, cacao butter, and hydrogenated oil; absorption enhancers such as a quaternary ammonium salt and sodium lauryl sulfate; moisturizers such as glycerol and starch; adsorbents such as starch, lactose, kaoline, bentonite, and colloidal silicic acid; and lubricants such as purified talc, a stearic acid salt, boric acid powder, and polyethylene glycol. Furthermore, tablets may optionally be prepared as tablets with an ordinary coating such as sugar-coated tablets, gelatin-protective tablets, enteric-coated tablets, film coated tablets, double layered tablets, and multilayered tablets. The pills may be prepared by using, as carriers, for example, excipients such as glucose, lactose, starch, cacao oil, hardened vegetable oil, kaoline, and talc; binders such as powdered acacia, powdered tragacanth, gelatin, and ethanol; disintegrators such as laminaran powder and agar powder and the like. Capsules may be manufactured according to ordinary methods by mixing with the above exemplified various carriers and then filling the mixture in hard gelatin capsules, soft capsules or the like. When oral liquid preparations are prepared, orally administrable solutions, syrups, elixirs and the like may be manufactured by an ordinary method by using flavor-corrective agents, buffering agents, stabilizers, smell-corrective agents and the like. In the above preparations, examples of the flavor-corrective agents include sucrose, bitter orange peel, citric acid, tartaric acid and the like, examples of the buffering agents include sodium citrate and the like, and examples of the stabilizers include tragacanth, gum arabic, gelatin and the like. The suppositories may be prepared by using, as carriers, for example, polyethylene glycol, cacao butter, higher alcohols, esters of higher alcohols, gelatin, semisynthetic glycerides, and the like. In preparing injections, it is preferred that the solution, emulsion and suspension are sterilized, and further isotonic with blood. As diluents used in these preparations, water, an aqueous solution of lactic acid, ethyl alcohol, propylene glycol, macrogol, ethoxylated isostearyl alcohol, polyoxyethylenated isostearyl alcohol, polyoxyethylene sorbitan fatty acid esters, and the like may be used. In such cases, saline, glucose or glycerin may be used in the pharmaceutical preparation in an amount sufficient to prepare an isotonic solution. Moreover, solubilizers, buffers, soothing agents, and the like, may be added. Furthermore, the aforementioned preparations may optionally be added with colorants, preservatives, perfumes, flavoring agents, sweetening agents and the like, or other drugs. The amount of Compound (I) or a pharmaceutically acceptable salt thereof contained in the pharmaceutical preparation of the present invention, is not particularly limited, but suitably selected, preferably usually 0.01 to 70% by weight of the pharmaceutical preparation.

The administration method of the medication of the present invention is not particularly limited, but suitably determined depending on dosage forms, the age, sex, and other conditions of a patient, severity of symptoms of the patient, and the like. For example, tablets, pills, powders, granules, capsules, solutions, suspensions and emulsions are orally administered. Injections are intravenously administered alone or in combination with usual replacement fluid such as glucose, amino acids, and the like, and further if needed, administered alone intraarterially, intramuscularly, intracutaneously, subcutaneously, or intraperitoneally. Suppositories are administered intrarectally.

The dose of the active ingredient of the medication of the present invention can be suitably selected depending on the dosing regimen, the age, sex, and other conditions of a patient, severity of the disease, and the like. The dose of Compound (I) or a pharmaceutically acceptable salt thereof is generally about 0.01 to 1000 mg/kg/day, preferably about 0.1 to 100 mg/kg/day. In addition, the preparation of the present invention may be administered once daily or in 2 to 4 divided doses per day.

EXAMPLES

The present invention will next be described in more detail by way of examples, which should not be construed as limiting the invention thereto.

Formulation Example 1

| | |
|---|---|
| Compound (1) | 25.0 mg |
| Lactose | 8.0 mg |
| Crystalline cellulose | 4.0 mg |
| Magnesium stearate | 1.0 mg |
| Talc | 1.0 mg |
| Corn Starch | 3.5 mg |
| Hydroxypropylmethyl cellulose | 2.5 mg |
| Per 1 tablet | 45.0 mg |

A tablet was prepared in a conventional manner according to the above formulation.

Formulation Example 2

| | |
|---|---|
| Compound (1) | 50.0 mg |
| Lactose | 85.0 mg |
| Corn Starch | 100.0 mg |
| Hydroxypropylmethyl cellulose | 3.0 mg |
| Per 1 Package | 238.0 mg |

Granules were prepared in a conventional manner according to the above formulation.

| | |
|---|---|
| Compound (1) | 50.0 mg |
| Lactose | 24.0 mg |
| Crystalline cellulose | 13.0 mg |
| Magnesium stearate | 1.0 mg |
| Per 1 Capsule | 88.0 mg |

A capsule was prepared in a conventional manner according to the above formulation.

Formulation Example 4

Injection

| | |
|---|---|
| Compound (1) | 50.0 mg |
| Distilled water for injection | q.s. |
| Per 1 Ampule | 5 mL |

An ampule was prepared in a conventional manner according to the above formulation per 1 ampule.

Formulation Example 5

Suppository

| | |
|---|---|
| Compound (1) | 100.0 mg |
| Witepsol W-35 (Trade name, product of Dynamit Nobel AG) | 1400.0 mg |
| Per 1 suppository | 1500.0 mg |

A suppository was prepared in a conventional manner according to the above formulation per 1 suppository.

Example 1

Actions in TNBS-Induced IBD Model

In this test, Compound (1) (50 mg/kg) was orally administered every day to TNBS-induced colitis mouse, which is a Crohn's disease model according to the method described in Biochemical and Biophysical Research Communications, 329, (2005), 1217-1224, and anti-inflammatory actions thereof were evaluated.

Ten 8-week-old male BALB/c mice (Japan SLC, Inc.) per one group were fasted for 24 hours, and anesthetized with diethyl ether. 2.0 g of TNBS (2,4,6-trinitrobenzene sulfonic acid) (Tokyo Chemical Industry CO., LTD.) diluted in 1 mL of 50% ethanol was intraintestinally infused to the mice with a vinyl-made catheter inserted into 2.5 cm from the rectum. The mice were held by the tail for 30 seconds after the intestinal infusion to prevent immediate leakage of the TNBS solution infused from the rectum. In control group, 1 mL of physiological saline instead of TNBS was intraintestinally infused to the mice. All of the mice were sacrificed with carbon dioxide 7 days after the intestinal infusion of TNBS or physiological saline, and dissected. In Compound (1) administration group, Compound (1) (50 mg/kg) was orally administered every day from the previous day of the intestinal infusion of TNBS. In the control group and Compound (I) non-administration group, drinking water was orally administered every day from the previous day of the intestinal infusion. After the completion of the administration period, the extracted large intestines of the mice were cut every 1 cm in the horizontal axis direction, and fixed in 10% formalin, followed by embedment in paraffin to perform HE staining. Based on Histological score (Table 1), observation of inflammation was converted into numbers.

Figure 2:
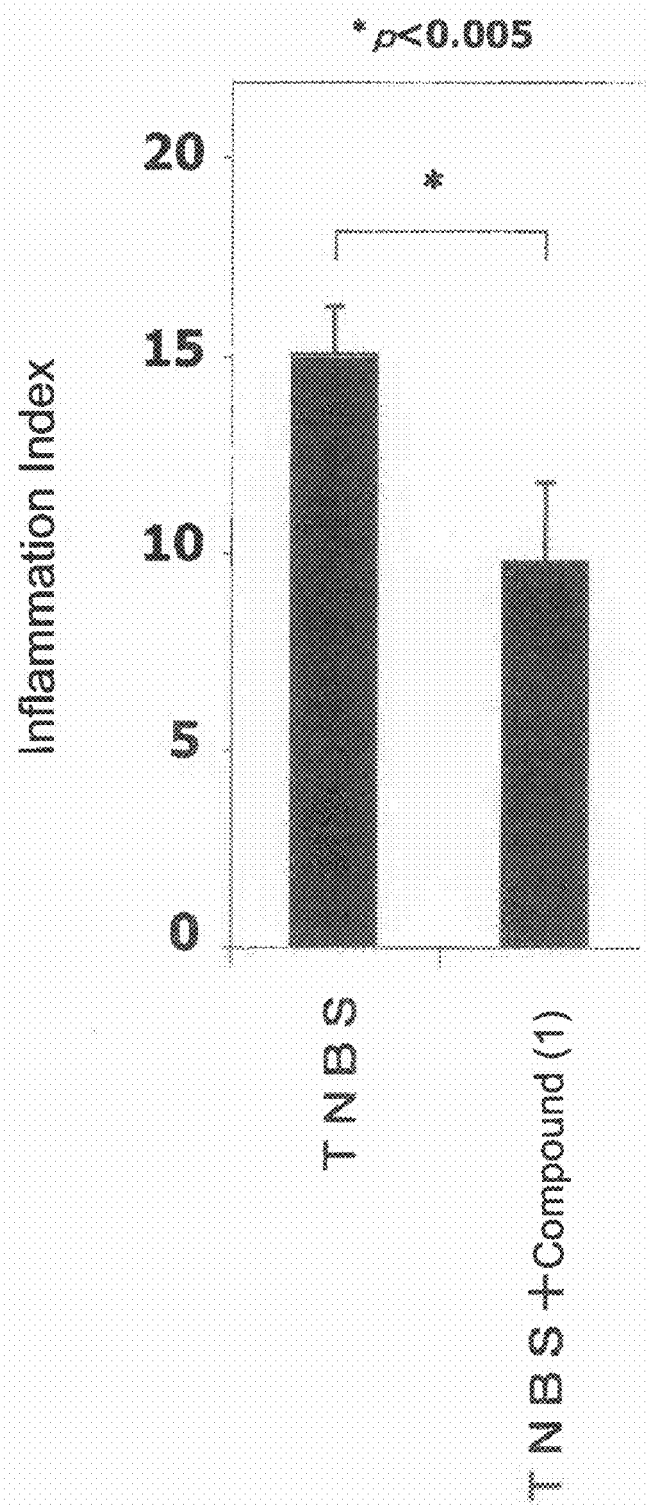
FIG. 2 shows inflammation index in TNBS-induced colitis mouse.

With intestinal infusion of TNBS, infiltration of inflammatory cells or shedding of the mucous membrane appeared in comparison with the control in which physiological saline was intraintestinally infused (FIG. 1). In the TNBS 2.0 mg administration group, transmural infiltration of inflammatory cells, shedding of the mucous membrane in the wide range, high degree edema, and loss of crypt were observed, while the range and degree of inflammation were mild in the Compound (1) administration group (FIG. 1) in spite of infiltration of inflammatory cells and shedding of the mucous membrane. By using Histological score (Table 1), the degree of inflammation was converted into numbers, and was investigated in comparison between the Compound (1) administration group and the Compound (I) non-administration group (FIG. 2). The scores decreased significantly in the Compound (1) administration group in comparison with the Compound (1) non-administration group (TNBS 2.0 mg: 15.0±1.2 points, TNBS+Compound (I): 9.8±2.1 points).

TABLE 1

| Histological score | |
| --- | --- |
| Extent of inflammation | 0 = normal, 1 = <10%, 2 = 10%, 3 = 10%-50%, 4 = >50% |
| Depth of the ulcer | 0 = no ulcer, 1 = mucosal involvement, 2 = mucosal + submucosal involvement<br>3 = penetration of muscularis propria, 4 = full thickness involvement |
| Infiltration of inflammatory cell | 0 = normal, 1 = weak, 2 = moderate, 3 = severe |
| Edema | 0 = normal, 1 = weak, 2 = moderate, 3 = severe |
| Crypt loss | 0 = normal, 1 = <10%, 2 = 10%, 3 = 10%-50%, 4 = >50% |
| Location of fibrosis | 0 = normal, 1 = mucosa only,<br>2 = mucosa + submucosa, 3 = including muscle layer,<br>4 = full thickness fibrosis |

Score ranges from 0 to a maximum of 22 points

Example 2

Figure 3:
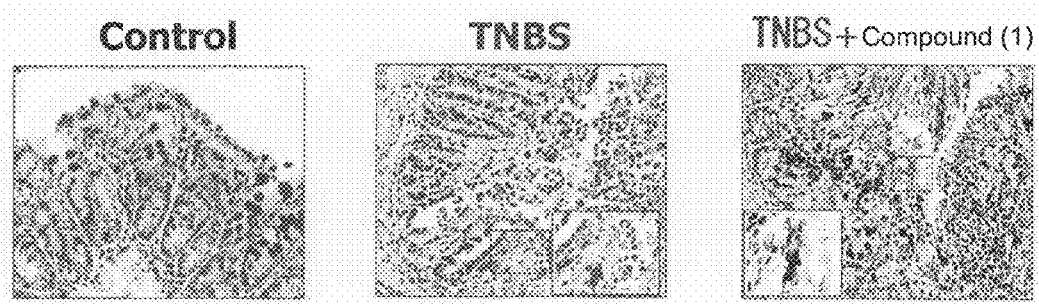
FIG. 3 shows an inhibitory action of apoptosis in intestinal epithelial cells by administration of Compound (1) in TNBS-induced colitis mouse.
Figure 4:
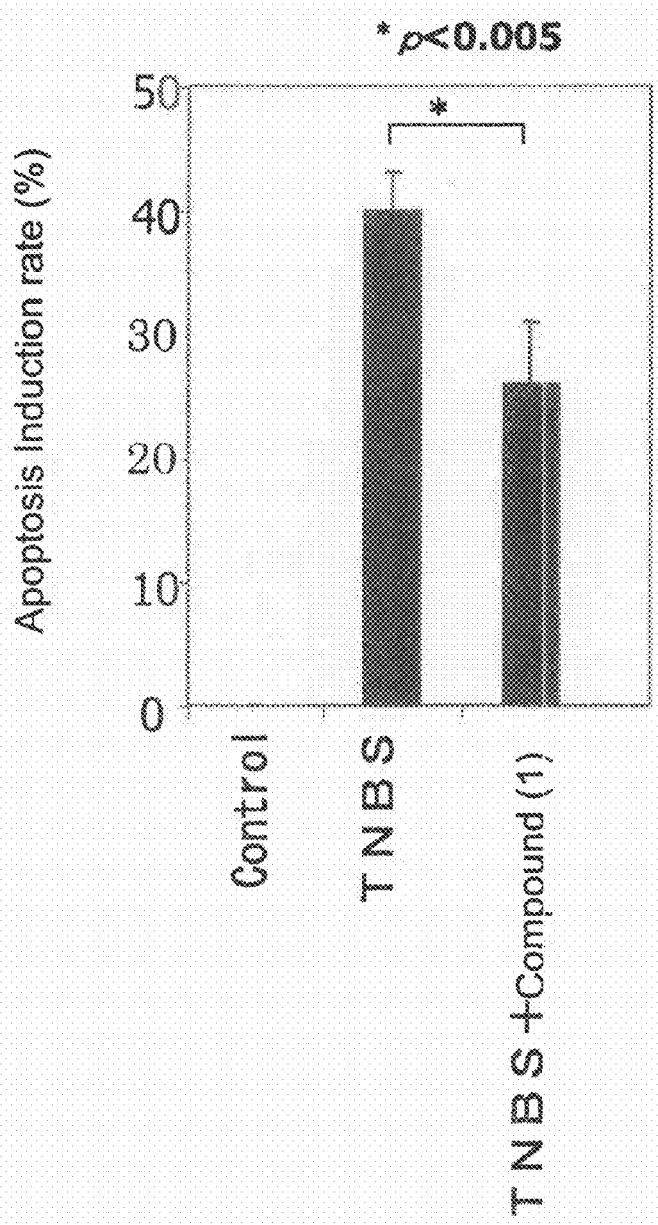
FIG. 4 shows apoptosis induction rate in TNBS-induced colitis mouse.

Inhibition of apoptosis of large intestinal epithelial cells in TNBS-induced colitis Large intestine affected by TNBS-induced colitis was subjected to Giemsa staining to stain the nucleus, and apoptosis of the intestinal epithelial cells was investigated (FIG. 3). Cells showing cell shrinkage or nucleus fragmentation were taken as apoptoic cells. 1000 cells in each segment were observed under the microscope, and the ratio of apoptotic cells (the apoptosis induction rate) was calculated (FIG. 4). It was shown that administration of Compound (1) significantly inhibited apoptosis of intestinal epithelial cells in TNBS-induced colitis (TNBS: 40.0±3.0%, TNBS+Compound (1): 26.0±5.0%.).

Example 3

Actions of Improving the Clinical Conditions in DSS-Induced IBD Model

This test was performed according to the method described in PEDIATRIC RESEARCH, Vol. 53, No. 1, 143 to 147, 2003. In particular, mice (6-week-old, C57BL/6N Jcl, CLEA Japan, Inc.) were divided into groups of eight mice each such that average body weight was the same in each group on Day 0. Dextran sulfate sodium (hereinafter, DSS, Wako Pure Chemical Industries, Ltd.) was dissolved in purified water and adjusted to 3% w/v, and the mice were allowed to free drinking of the solution from the water supply bottle for 5 days (Day 0 to Day 4), to thereby prepare the ulcerative colitis model. The following experimental groups were established: no drug administration group (Control), 100 mg/kg/day of Compound (1) administration group, and 100 mg/kg/day of 5-aminosalycilic acid (hereinafter, 5-ASA) administration group and 5 mg/kg/day of prednisolone administration group as comparative drug administration groups (wherein, the dosage of the comparative drug was pharmacologically effective dose). Furthermore, no treatment group was established in which purified water was used for drinking instead of 3% DSS aqueous solution. Each drug was administered from 4 days after the initiation of drinking of 3% DSS aqueous solution for 7 days (Day 4 to Day 10). Determination was made on the next day of the last administration of each drug (Day 11). As the evaluation index, the length of the large intestine and the rate of body weight change from the first day of the test (Day 0) to the last day of the test (Day 11) were measured.

The length of the large intestine in the control group on the determination day was 73.4% relative to that of the no treatment group, which showed significant shrinkage. The lengths of the large intestine in the Compound (1) administration group and the prednisolone administration group were 88.6% and 93.2%, respectively, relative to that of the no treatment group. Such lengths of the large intestine were significantly longer, respectively, than that of the control group, showing improvement of the clinical conditions. The length of the large intestine in the 5-ASA administration group was 80.3% relative to that of the control group, showing no significant difference, in spite of the tendency to improve the shrinkage of the large intestine.

On the other hand, with regard to the rate of body weight change from the first day of the test to the determination day, the control group had a weight loss of 1.7±1.8%, whereas Compound (1) administration group had a slight weight gain of 0.4±1.2%. However, the prednisolone administration group and 5-ASA administration group had weight losses of 3.9±1.0% and 5.0±0.3%, respectively, which were higher than that of the control group and were assumed due to the adverse effects of the drugs.

These results suggest that Compound (1) has excellent balance between therapeutic effects and adverse effects in comparison with the conventional therapeutic agents for inflammatory bowel disease, and is useful as a therapeutic agent for ulcerative colitis.

TABLE 2

Changes in length of the large intestine and body weight in DSS-induced IBD model animals

| | Change in length of the large intestine (Ratio to the no treatment group, %) | Rate of body weight change (%, Mean ± SE) |
|---|---|---|
| No treatment | 100 | 3.7 ± 1.5 |
| Control | 73.4 | −1.7 ± 1.8 |
| 100 mg/kg/day Compound (I) | 88.6 | 0.4 ± 1.2 |
| 5 mg/kg/day Prednisolone | 93.2 | −3.9 ± 1.0 |
| 100 mg/kg/day 5-ASA | 80.3 | −5.0 ± 0.3 |

* A group which showed significant improvement in the length of the large intestine compared with the control group ($P < 0.05$, student-t test).

Example 4

Single Dose Oral Toxicity Test 2000 mg/kg of Compound (1) was suspended in 0.5% HPMC solution, and orally administered at a single dose of 10 mL/kg to five male and five female SD rats (6-week-old). As a result, no case of death was observed, and no body weight change was also observed.

The invention claimed is:

1. A method of treating inflammatory bowel disease, which comprises administering to a patient with inflammatory bowel disease an effective amount of 5-chloro-6-(2-iminopyrrolidin-1-yl)methyl-2,4(1H,3H)-pyrimidinedione or a pharmaceutically acceptable salt thereof.

2. The method according to claim 1, wherein the inflammatory bowel disease is ulcerative colitis or Crohn's disease.

3. The method according to claim 1 or 2, wherein the 5-chloro-6-(2-iminopyrrolidin-1-yl)methyl-2,4(1H,3H)-pyrimidinedione or a pharmaceutically acceptable salt thereof is 5-chloro-6-(2-iminopyrrolidin-1-yl) methyl-2,4(1H,3H)-pyrimidinedione hydrochloride.

* * * * *